United States Patent [19]

Baus et al.

[11] Patent Number: 5,049,678
[45] Date of Patent: Sep. 17, 1991

[54] 1-HYDROXY-1,2,4-TRIAZOLES

[75] Inventors: Ulf Baus, Dossenheim; Wolfgang Reuther, Heidelberg, both of Fed. Rep. of Germany

[73] Assignee: BASF Aktiengesellschaft, Ludwigshafen, Fed. Rep. of Germany

[21] Appl. No.: 445,433

[22] Filed: Dec. 4, 1989

[30] Foreign Application Priority Data

Jan. 7, 1989 [DE] Fed. Rep. of Germany ....... 3900347

[51] Int. Cl.$^5$ .......................................... C07D 249/12
[52] U.S. Cl. .............................. 548/263.2; 548/263.8; 548/269.4
[58] Field of Search ............... 548/263.2, 263.8, 262.2, 548/269.4

[56] References Cited

U.S. PATENT DOCUMENTS 3,912,752 10/1975 Meiser et al. ........................ 514/383
3,952,002 4/1976 Kramer et al. ........................ 514/383

FOREIGN PATENT DOCUMENTS 59288 4/1967 Fed. Rep. of Germany .
3820738 12/1989 Fed. Rep. of Germany .
3820739 12/1989 Fed. Rep. of Germany .

OTHER PUBLICATIONS

Schofield et al., "The Azoles", Cambridge Univ. Press, 1976, p. 126.
Kunz et al., "(Halomethyl)Traizoles", CA 98:53908g, 1983.
Pevzner et al., "Heterocyclic Nitro Compounds, etc." CA 93:46530w (1980).
Chemical Abstracts, vol. 105, No. 17, Oct. 27, 1986, 152 441u.
Chemical Abstracts, vol. 107, No. 21, Nov. 23, 1987, 191 136j.
Wickings et al., "Non-Steroidal Inhibition, etc." Steroid Biochem, 26, pp. 641-646 (1987).
Crom et al., "Organic Chemistry" NY:McGraw-Hill Co., 1964, pp. 243 and 250.

Primary Examiner—Mary C. Lee
Assistant Examiner—Patricia L. Morris
Attorney, Agent, or Firm—John H. Shurtleff

[57] ABSTRACT 1-hydroxy-1,2,4-traizoles have the general formula I

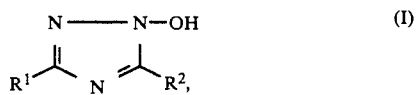

where $R^1$ and $R^2$ are singly independently of the other hydrogen, alkyl, halogen or substituted or unsubstituted aryl or together an alkylene chain.

3 Claims, No Drawings

1-HYDROXY-1,2,4-TRIAZOLES

The present invention relates to novel 1-hydroxy-1,2,4-triazoles and the preparation thereof.

DE-A-2,201,063 and DE-A-2,324,010 disclose useful bioactive 1-substituted 1,2,4-triazoles.

DE-A-3,820,738 and DE-A-3,820,739 disclose processes for preparing 1-hydroxypyrazoles with peroxy compounds.

It is an object of the present invention to provide novel intermediates for simple access to novel 1-substituted 1,2,4-triazoles.

We have found that this object is achieved by the novel 1-hydroxy-1,2,4-triazoles of the general formula I

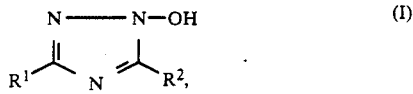

where
R$^1$ and R$^2$ are singly independently of one another hydrogen, alkyl, halogen or substituted or unsubstituted aryl or together an alkylene chain.

The substituents are R$^1$ and R$^2$ on the 1-hydroxy-1,2,4-triazoles I, on any salt intermediate III and on precursors thereof, namely 1-H-1,2,4-triazoles II, have independently of each other the following meanings:
hydrogen,
alkyl such as C$_1$-C$_{20}$-alkyl, preferably C$_1$-C$_8$-alkyl, particularly preferably C$_1$-C$_4$-alkyl such as methyl, ethyl, n-propyl, isopropyl, n-butyl, isobutyl, sec.-butyl or tert.-butyl,
halogen, such as fluorine, chlorine, bromine or iodine, preferably chlorine, bromine or iodine, particularly preferably chlorine,
aryl such as phenyl, 1-naphthyl, 2-naphthyl, 1-anthranyl, 2-anthranyl or 9-anthranyl, preferably phenyl, 1-naphthyl or 2-naphthyl, particularly preferably phenyl,
alkyl- and/or halogen- monosubstituted, disubstituted or trisubstituted aryl, preferably C$_1$-C$_8$-alkyl and-/or fluorine-, chlorine-, bromine- or iodine-monosubstituted, -disubstituted or -trisubstituted phenyl, particularly preferably C$_1$-C$_4$-alkyl and/or fluorine-, or chlorine- monosubstituted, -disubstituted or trisubstituted phenyl such as 2-fluorophenyl, 4-fluorophenyl, 2-chlorophenyl, 4-chlorophenyl, 2,4-difluorophenyl, 2,4-dichlorophenyl, 2-chloro-4-fluorophenyl, 2,4,6-trifluorophenyl or 2,4,6-trichlorophenyl.

The substituents R$^1$ and R$^2$ in the compounds I, II and III can also represent together an alkylene chain which may be substituted by alkyl, halogen and/or substituted or unsubstituted aryl. The preferred substituents on the alkylene chain are analogous to those mentioned above. The alkylene chain consists of 4 or 5 links; that is, it is —(CH$_2$)$_4$— or —(CH$_2$)$_5$—, preferably the latter.

In the compounds III, ME⊕ is an alkali metal or alkaline earth metal cation, preferably lithium, sodium, potassium, magnesium or calcium, particularly preferably lithium, sodium or potassium.

Preferred 1-hydroxy-1,2,4-triazoles I and preferred 1-H-1,2,4-triazoles II are:

| 1-Hydroxy-1,2,4-triazoles I | 1-H-1,2,4-triazoles II |
|---|---|
| 1-hydroxy-1,2,4-triazole | 1-H-1,2,4-triazole |
| 1-hydroxy-3-methyl-1,2,4-triazole | 1-H-3-methyl-1,2,4-triazole |
| 1-hydroxy-5-methyl-1,2,4-triazole | 1-H-5-methyl-1,2,4-triazole |
| 1-hydroxy-3,5-dimethyl-1,2,4-triazole | 1-H-3,5-dimethyl-1,2,4-triazole |
| 1-hydroxy-3-ethyl-1,2,4-triazole | 1-H-3-ethyl-1,2,4-triazole |
| 1-hydroxy-5-ethyl-1,2,4-triazole | 1-H-5-ethyl-1,2,4-triazole |
| 1-hydroxy-3,5-diethyl-1,2,4-triazole | 1-H-3,5-diethyl-1,2,4-triazole |
| 1-hydroxy-3-ethyl-5-methyl-1,2,4-triazole | 1-H-3-ethyl-5-methyl-1,2,4-triazole |
| 1-hydroxy-5-ethyl-3-methyl-1,2,4-triazole | 1-H-5-ethyl-3-methyl-1,2,4-triazole |
| 1-hydroxy-3-chloro-1,2,4-triazole | 1-H-3-chloro-1,2,4-triazole |
| 1-hydroxy-5-chloro-1,2,4-triazole | 1-H-5-chloro-1,2,4-triazole |
| 1-hydroxy-3,5-dichloro-1,2,4-triazole | 1-H-3,5-dichloro-1,2,4-triazole |
| 1-hydroxy-3,5-diphenyl-1,2,4-triazole | 1-H-3,5-diphenyl-1,2,4-triazole |
| 1-hydroxy-3-(4-fluorophenyl)-1,2-triazole | 1-H-3-(4-fluorophenyl)-1,2,4-triazole |

Particular preference is given to 1-hydroxy-1,2,4-triazoles as compound I and 1-H-1,2,4-triazoles as compound II.

The 1-hydroxy-1,2,4-triazoles I are obtainable by the following methods:

The reaction takes place between a 1-H-1,2,4-triazole II and a peroxy compound at −20° C. to +150° C. in the presence or absence of an agent which by salt formation leads via III to the 1-hydroxy-1,2,4-triazole I in accordance with the following reaction equation:

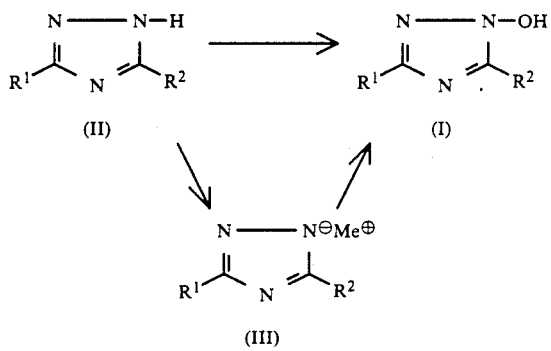

If the 1-H-1,2,4-triazoles II are reacted with peroxy compounds in the absence of a salt-forming agent, the procedure is as follows:

From 1 to 3 mole equivalents of 1-H-1,2,4-triazole II are admixed in a solvent such as water, water/acetone mixture, tetrahydrofuran, diglyme, methyl chloride or chloroform with 1 mole equivalent of peroxycarboxylic acid, preferably with m-chloroperbenzoic acid. The reaction temperature is within the range of from 0° to 50° C., room temperature is preferred.

If the 1-H-1,2,4-triazoles are reacted with peroxy compounds in the presence of a salt-forming agent, the procedure is as follows:

a) From 1 to 10 mole equivalents of 1-H-1,2,4-triazole II are metallated in an inert solvent such as diglyme, tetrahydrofuran or diethyl ether with an organo-metallic compound, an alkali metal suspension or a hydride and then admixed with 1 mole equivalent of dibenzoyl peroxide. The mixture is stirred at room temperature for several days.

b) From 1 to 3 mole equivalents of 1-H-1,2,4-triazole II are methylated in water with a hydroxide, a carbonate or a bicarbonate and then admixed with 1 mole equivalent of peroxycarboxylic acid and stirred overnight. Instead of the peroxycarboxylic acid it is also possible to use the alkali metal or alkaline earth metal salt of the peroxycarboxylic acid and add it for example in the solid form.

Suitable salt-forming agents are organometallic compounds, e.g. metal alkyls such as n-butyllithium, tert.-butyllithium or methyllithium or metal aryls such as phenyllithium, alkali metal suspensions, e.g. sodium in toluene or potassium in toluene, hydrides, e.g. alkali metal hydrides such as lithium hydride, sodium hydride and potassium hydride or alkaline earth metal hydrides such as calcium hydride, preferably sodium hydride, hydroxides, e g. alkali metal hydroxides such as lithium hydroxide, sodium hydroxide, potassium hydroxide or alkaline earth hydroxides such as calcium hydroxide and magnesium hydroxide, carbonates, e.g. alkali metal carbonates such as lithium carbonate, sodium carbonate and potassium carbonate, alkaline earth metal carbonates such as calcium carbonate and magnesium carbonate, and bicarbonates, e.g. sodium bicarbonate.

These reactions can preferably also be carried out in the presence of a solvent. If organometallics or hydrides are used, suitable solvents are ethers such as diethyl ether, methyl butyl ether, tetrahydrofuran and dioxane, glycol ethers such as diglyme and triglyme, aliphatic hydrocarbons such as pentane, hexane, petroleum ether and cyclohexane, aromatic hydrocarbons such as benzene, toluene and xylenes, and mixtures thereof.

If hydroxides, carbonates or bicarbonates are used, suitable solvents are water, alcohols such as methanol, methanol, n-propanol, isopropanol and the butanols, ketones such as acetone and diethyl ketone, and mixtures thereof, preferably water.

Suitable peroxy compounds are organic peroxides, for example dialkylperoxides, alkyl aryl peroxides, diaryl peroxides, diacyl peroxides, e.g. diacetyl peroxide, dipropionyl peroxide and dibenzoyl peroxide, preferably dibenzoyl peroxide; peroxy acids, for example peroxysulfonic acids, e.g. p-tolueneperoxysulfonic acid, tolueneperoxysulfonic acid, p-bromotolueneperoxysulfonic acid and methylperoxysulfonic acid, preferably p-toluenesulfonic acid, peroxycarboxylic acids such as peracetic acid, perbenzoic acid, m-chloroperbenzoic acid, peroxypropionic acid, peroxybutyric acid, peroxymaleic acid, monoperoxysuccinic acid and monoperoxyphthalic acid, preferably monoperoxyphthalic acid.

The 1-hydroxy-1,2,4-triazoles II are useful intermediates for bioactive substances such as fungicides, growth regulators and biocides.

EXAMPLE 1

103.5 g (1.5 mol) of 1-H-1,2,4-triazole were dissolved in 1344 g (12 mol) of 50% strength aqueous potassium hydroxide. 340 g (3 mol) of 30% strength $H_2O_2$ were added with ice-cooling, followed by 555 g (3.75 mol) of phthalic anhydride a little at a time, and the mixture was stirred at room temperature (20° to 30° C.) for 2 hours. The mixture was then acidified with approximately 35% sulfuric acid to pH<1.5, the resulting precipitate was filtered off with suction, and the filtrate was analyzed by quantitative HPLC. 19 g (15%) were obtained, and worked up in a conventional manner; melting point: 132° C.

We claim:

1. A 1-hydroxy-1,2,4-triazole of the formula

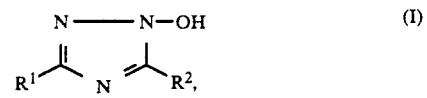

wherein $R^1$ and $R^2$ are each independently of the other hydrogen, $C_1$-$C_{20}$-alkyl, fluorine, chlorine, bromine, phenyl, 1-naphthyl, 2-naphthyl, or phenyl bearing from 1 to 3 substituents selected from the group consisting of halogen and $C_1$-$C_8$-alkyl.

2. A 1-hydroxy-1,2,4-triazole of the formula I as claimed in claim 1, wherein $R^1$ and $R^2$ are each independently of the other hydrogen, $C_1$-$C_8$-alkyl, chlorine, unsubstituted phenyl or phenyl bearing from 1 to 3 substituents selected from the group consisting of fluorine, chlorine and $C_1$-$C_4$-alkyl.

3. 1-hydroxy-1,2,4-triazole.

* * * * *